(12) United States Patent
Chastain et al.

(10) Patent No.: US 6,178,356 B1
(45) Date of Patent: Jan. 23, 2001

(54) CORONARY VENOUS LEAD HAVING FIXATION MECHANISM

(75) Inventors: Stuart A. Chastain, Shoreview; Bruce A. Tockman, Scandia; Randy W. Westlund, Minneapolis; Lili Liu, Little Canada, all of MN (US)

(73) Assignee: Cardiac Pacemakers, Inc., St. Paul, MN (US)

( * ) Notice: Under 35 U.S.C. 154(b), the term of this patent shall be extended for 0 days.

(21) Appl. No.: 09/280,128

(22) Filed: Mar. 26, 1999

Related U.S. Application Data

(62) Division of application No. 09/027,288, filed on Feb. 20, 1998, now Pat. No. 5,931,864.

(51) Int. Cl.[7] ........................................... A61N 1/05
(52) U.S. Cl. ................................................. 607/128
(58) Field of Search .................... 607/122, 126, 607/128, 130

(56) References Cited

U.S. PATENT DOCUMENTS

| | | |
|---|---|---|
| 3,902,501 | 9/1975 | Citron et al. . |
| 4,269,198 | 5/1981 | Stokes . |
| 4,301,815 | 11/1981 | Doring . |
| 4,407,303 | 10/1983 | Akerstrom . |
| 4,628,944 | 12/1986 | MacGregor et al. . |
| 4,796,643 * | 1/1989 | Nakazawa et al. ................. 607/128 |
| 5,256,146 | 10/1993 | Ensminger et al. . |
| 5,531,781 * | 7/1996 | Alferness et al. ................. 607/126 |
| 5,531,783 * | 7/1996 | Giele et al. ....................... 607/126 |
| 5,545,206 | 8/1996 | Carson . |

\* cited by examiner

*Primary Examiner*—George R. Evanisko
(74) *Attorney, Agent, or Firm*—Nikolai, Mersereau & Dietz, P.A.

(57) ABSTRACT

A body implantable lead for placement in a selected coronary vein includes a resilient retention structure for inhibiting displacement of the lead because of heart beat action, breathing or other body movement. The retention structure includes a plurality of resilient projections that are attached to the lead body and which are adapted to project at a predetermined acute angle to the axis of the lead body when unconstrained. Prior to being routed through the vascular system, the projections can be bonded to the lead body to provide a low profile with a biodegradable adhesive. Following exposure to body fluids, the adhesive dissolves, releasing the projections so that they can engage the walls of the vein in which the lead is disposed.

7 Claims, 2 Drawing Sheets

CORONARY VENOUS LEAD HAVING FIXATION MECHANISM

This is a Divisional of application Ser. No. 09/027,288, filed on Feb. 20, 1998 now U.S. Pat. No. 5,931,864.

BACKGROUND OF THE INVENTION

I. Field of the Invention

This invention relates generally to a cardiac pacing lead designed for placement in a left coronary vein, and more particularly to such a lead employing tines for holding the distal end portion of the pacing lead in place.

II. Discussion of the Prior Art

Cardiac pacemakers for treating bradycardia commonly employ pacing leads for connecting an electrical pulse generator to excitable cardiac tissue, usually within the heart's right ventricle. Such leads have one or more electrodes proximate the distal end thereof and also commonly employ tines located just distal of the tip electrode for holding that electrode in contact with endocardial tissue in the right ventricle. The tines engage the trabeculae, resisting movement of the lead tip due to body movement and/or contractions of the heart muscle itself.

More recently, researchers have found that cardiac stimulation can have a beneficial effect in treating patients suffering from congestive heart failure (CHF). By properly controlling the AV interval of the pacemaker, a sick heart may be made to pump more efficiently. Pacing therapy for the treatment of CHF, however, often requires the ability to stimulate the left ventricle, either alone or in conjunction with right ventricular stimulation. Current methods for achieving left ventricular pacing require placement of an epicardial lead, via thoracotomy or a thoracoscopic approach. Because of the usual poor condition of CHF patients, both of these procedures are "high risk" due to the trauma of the surgery itself and the need for general anesthesia. To obviate the need for a thoracotomy, left ventricular access (LVA) leads have been developed that may be introduced through the coronary sinus and then advanced through the coronary veins so that the lead's stimulating tip electrode can be positioned on the surface of the left ventricle near the apex of the heart.

Those skilled in the art knowing the anatomical configuration and dimensions of the coronary veins on the left side of the heart can appreciate that a lead to be routed therethrough must be of a relatively small diameter as compared to a conventional pacing lead adapted for placement in the right ventricle. As such, a means must be provided for at least temporarily anchoring the electrode at a desired selected location until fibrotic attachment and resulting lead stabilization occurs. Heart motion and respiratory motion as well as blood flow or other body movement are typical mechanisms for lead dislodgement. The problem is also deemed to be more acute in CHF patients due to the dilated condition of CHF hearts.

It can be seen, then, that a need exists for a pacing lead that can readily be advanced through the coronary sinus and thence through a coronary vein on the left side of the heart and having an anchoring structure for maintaining the electrode at a desired site notwithstanding heart motion, respiratory motion blood flow and other body movement.

SUMMARY OF THE INVENTION

The present invention comprises an implantable lead for placement in a selected coronary vein. It includes a lead body with at least one electrode carried thereon at a distal portion thereof and an elongated conductor contained within the lead body electrically joining a terminal pin at a proximal end of the lead body to the electrode at its distal end. To temporarily anchor the distal end portion of the lead body within the selected coronary vein until such time that fibrosis can be relied upon for retention, the lead includes a plurality of resilient passive retention structures attached at one end to the lead body and adapted to project at a predetermined acute angle to an axis of the lead body when the resilient retention structures are unconstrained. The retention structures are designed to conform to the anatomy and provide retention by producing a slight amount of friction against the vessel wall. The retention structures can be constructed of a resorbable material that can be either molded as part of the lead or attached to the lead body by a collar or similar technique. The structure can be temporarily adhered to the lead body in part or in total. Partial adhesion allows parts of the retention structure to be fixed to lead body for a short period of time to, for example, provide a low profile during lead insertion. The biodegradable adhesive is used to temporarily constrain the retention structure to lie against the lead body until released by the action of body fluids on the biodegradable adhesive following placement of the electrode at the desired site. Total adhesion with a resorbable adhesive allows the lead body to be separated from the retention structure if an attempt is made at a latter date to extract the lead. Alternatively, the retention structure itself can be designed to break away during an extraction procedure.

The resorbable material can be a material such as polydioxanone, polyglactin or poliglecaprone.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
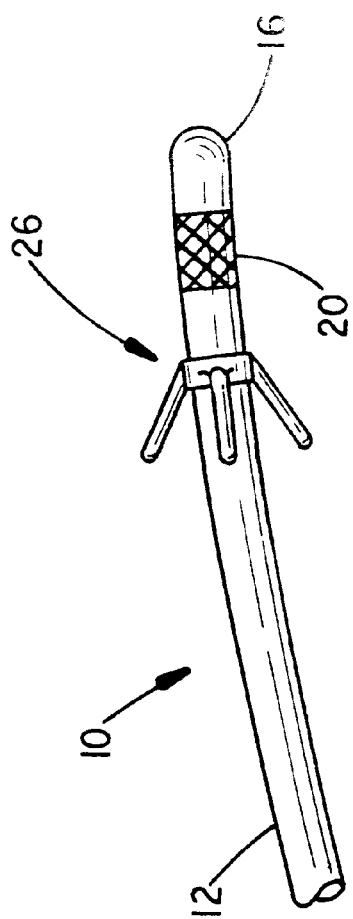
FIG. 1 is a partial perspective view of a pacing lead designed for placement in a coronary vein.
Figure 1:
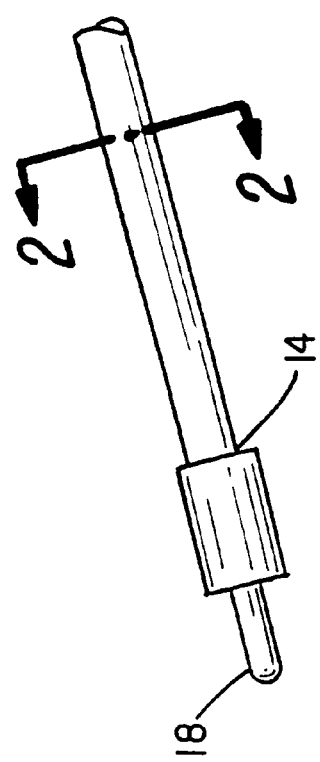

Referring to FIG. 1, there is indicated generally by numeral 10 a pacing lead specifically designed for placement within a selected coronary vein branch on the epicardium on the left side of the heart. It comprises a lead body 12 having a proximal end 14 and a distal end 16. Affixed to the proximal end of the lead is a terminal 18 adapted to mate with a connector port on a cardiac pacemaker with which the lead is used.

Affixed near to the distal end 16 of the lead is a stimulating electrode 20. While the lead 10 is shown as being a monopolar lead, it is also contemplated that one or more additional electrodes may be provided on the lead body to allow for bipolar pacing and sensing, all as is well known in the art.

Figure 2:
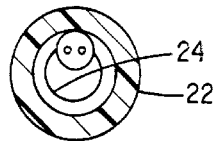
FIG. 2 is a cross-sectional view taken along the line 2—2 in FIG. 1.

As shown in the cross-sectional view of FIG. 2, the lead body 12 has an outer coating or jacket 22 of an electrically insulating material covering an electrical conductor 24 that extends the length of the lead body to connect the terminal pin 18 at the proximal end thereof to the electrode 20 at its distal end. Without limitation, the insulating sheath 22 may comprise silicone rubber or other biocompatible polymer. The inner conductor 24 may be a multi-filer helically wound structure or a cable conductor either of which can be fabricated from tantalum, titanium, titanium alloy, stainless steel alloy, cobalt nickel alloy or a combination of these materials. The wire can optionally be clad with a noble metal such as platinum or platinum/iridium alloy.

In accordance with the present invention, there is provided an anchoring means disposed on the distal end portion of the lead and which is identified generally by numeral 26 in FIG. 1. As can best be seen in the enlarged view of FIGS. 3 and 4, the anchoring means 26 may comprise an annular collar 28 dimensioned to closely surround the O.D. of the lead body and may be attached by means of a permanent or biodegradable adhesive. Alternatively, the anchoring means may be integral to lead. The free ends of the retention structure 30 may be adhesively bonded to the lead body 12, using a biodegradable adhesive 32, so that the retention structures are constrained to lie generally parallel to the longitudinal axis of the lead. The adhesive is such that when exposed to body fluids, it will release within a matter of minutes, allowing the resilient retention structures to deploy to the position shown in FIG. 4 so that the anchoring device exerts forces against the vein walls to adequately secure the lead in the desired implant site.

Figure 3:
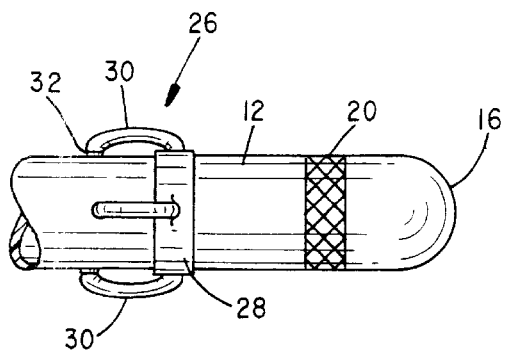
FIG. 3 is a greatly enlarged view of the distal end portion of the lead of FIG. 1 showing the retention structures prior to lead placement.
Figure 4:
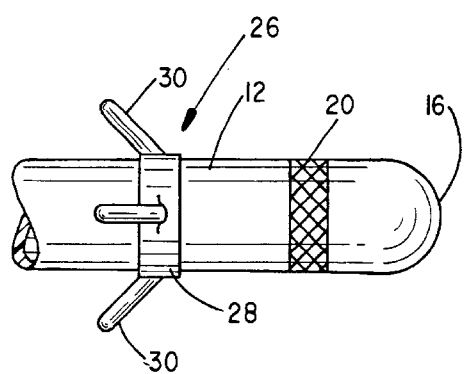
FIG. 4 is a view like that of FIG. 3 following placement and release of the retention structures.

The retention structures are designed such that their natural state is in the expanded condition shown in FIG. 4 and yet to have the appropriate geometric configuration and material properties to easily collapse along the lead body as shown in FIG. 3. This facilitates advancement of the lead through the vasculature or through any catheters which may be employed during lead deployment.

The retention structures may be comprised of a soft, biocompatible polymer, such as silicone rubber, of approximately 50 shore A durometer. Other materials which we have found suitable as retention structure material include filaments made from poliglecaprone, polyglactin, polydioxanone or other bioresorbable polymer. The number of surface projections or filaments comprising the retention structure can range from one to six but are not limited to this number. They extend from the surface of the lead 28 at an angle less than 90°, but generally greater than 20°, depending on the anticipated size of the venous vessel in which it is to be implanted. The length of the projections may vary as well, ranging from 0.025 in. to about 0.200 in., again depending on the size of the vessel in which the lead is to be implanted, the thickness and durometer of the material used to fabricate the projections. The projections may also be attached as a loop or loops rather than as single or multiple strands. Alternatively, the projections or filaments may be helically wound around the lead body.

Often when cardiac pacing leads require extraction, it occurs within weeks of original implantation. In the embodiment where the retention structure is not integral to the lead body, but constitutes an attachment, such as a collar, the biodegradable adhesive used to affix the collar 28 to the lead body 12 may be of a slower release time than the adhesive adhering the tips of the retention structures 30 to the lead body. For example, while the adhesive joining the free ends of the retention projections to the lead body may release within a matter of minutes, the adhesive used to join the collar 28 to the lead body may remain active for a period of several weeks. As such, a controlled timely detachment of the anchoring structure from the lead can be achieved. The adhesive, over time, is resorbed by the body, releasing the lead from the anchoring mechanism. This allows the lead to be more readily removed from a vein should that become necessary. By fabricating the collar 28 and the retention structures 30 from a resorbable polymer, the anchoring structure may reabsorb or may be left behind following lead removal and would ultimately be absorbed or degraded by the body but at a substantially slower rate than the resorbable adhesive that is used to attached the fixation feature to the lead.

Figure 5:
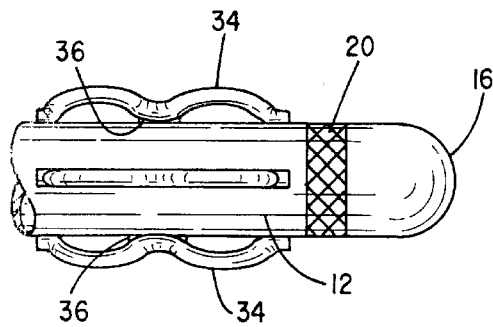
FIG. 5 is a greatly enlarged partial end view of a lead having an alternative anchoring arrangement prior to its implantation.
Figure 6:
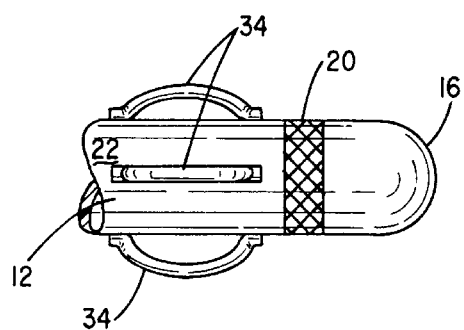
FIG. 6 is a view of the device of FIG. 5 at a time following implantation of the lead into the body.

FIGS. 5 and 6 illustrate a further embodiment of the invention in which the retention structures comprise resilient arches or bows 34 affixed to the polymer jacket 22 comprising the lead body 12. In FIG. 5, the arch is shown as being collapsed against the lead body 12 and held in place by a resorbable polymer adhesive as at 36. The polymer adhesive is designed to release following exposure to body fluids within a relatively short predetermined time interval, such as five minutes. This permits the lead to be routed through the vasculature with the retention projections in a collapsed form and the electrode 20 placed at a desired site within a vein branch on the left side of the heart. When the adhesive bond 36 releases, the resilient property of the polymer allows the retention structures to expand against the wall of the vein branch with a desired predetermined force.

It is also contemplated that these retention structures 34 be resorbable over time. As a further feature, a steroid additive may be added to the polymer comprising the retention structures and which is released during degradation to provide therapeutic activity. The steroid may also reduce encapsulation of the electrode so that less energy need be delivered by the pulse generator in order to ensure capture of the myocardial tissue.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. In a body implantable lead for placement in a selected coronary vein, the lead having a flexible lead body of an outer diameter permitting placement in the selected coronary vein, with at least one electrode carried by the lead body on a distal end portion thereof and an elongated conductor contained within the lead body and electrically connected to the one electrode, the improvement comprising:
   anchoring means including resilient retention structures integrally attached at one end and releasably attached at an opposite end to the lead body to form an arch, the retention structure adapted to project radially outward and proximally at a predetermined acute angle to an axis of the lead body when said opposite end is released.

2. The implantable lead of claim 1 wherein the retention structures are of a sufficient length and resiliency to engage a wall of the selected coronary vein with a force sufficient to resist movement of the electrode carried by the lead but insufficient to distort the wall of the selected coronary vein.

3. The implantable lead of claim 1 wherein the retention structures are made of a resorbable material.

4. The implantable lead of claim 3 wherein the resorbable material is selected from a group consisting of polydioxanone, polyglactin and poliglecaprone.

5. The implantable lead as in claim 1 wherein the retention structures comprise a filament.

6. The implantable lead as in claim 5 wherein the filament is a resorbable material.

7. The implantable lead of claim 1 wherein the retention structure is adhered to the lead body by a bioresorbable adhesive to allow the retention structure to lie parallel to the axis of the lead body.

\* \* \* \* \*